United States Patent
Mertoglu

(10) Patent No.: US 12,128,067 B2
(45) Date of Patent: Oct. 29, 2024

(54) NASAL SOLUTION WITH CLOSED BASIN NATURAL SPRING WATER CHARACTERISTIC AND METHOD FOR OBTAINING SAID NASAL SOLUTION

(71) Applicants: YILDIZ TEKNIK UNIVERSITESI, Istanbul (TR); Haci Murat Mertoglu, Bagcilar/Istanbul (TR)

(72) Inventor: Haci Murat Mertoglu, Bagcilar/Istanbul (TR)

(73) Assignees: YILDIZ TEKNIK UNIVERSITESI, Istanbul (TR); Haci Murat Mertoglu, Istanbul (TR)

( * ) Notice: Subject to any disclaimer, the term of this patent is extended or adjusted under 35 U.S.C. 154(b) by 556 days.

(21) Appl. No.: 17/297,238

(22) PCT Filed: Nov. 25, 2019

(86) PCT No.: PCT/TR2019/050993
§ 371 (c)(1),
(2) Date: May 26, 2021

(87) PCT Pub. No.: WO2020/112063
PCT Pub. Date: Jun. 4, 2020

(65) Prior Publication Data
US 2022/0000909 A1 Jan. 6, 2022

(30) Foreign Application Priority Data

Nov. 29, 2018 (TR) .................................. 2018/18237
Jan. 8, 2019 (TR) .................................. 2019/00230

(51) Int. Cl.
| | | |
|---|---|---|
| A61K 33/10 | (2006.01) | |
| A61K 9/08 | (2006.01) | |
| A61K 33/14 | (2006.01) | |
| A61K 9/00 | (2006.01) | |

(52) U.S. Cl.
CPC ................ *A61K 33/10* (2013.01); *A61K 9/08* (2013.01); *A61K 33/14* (2013.01); *A61K 9/0043* (2013.01)

(58) Field of Classification Search
CPC ........ A61K 33/10; A61K 9/0043; A61K 9/08; A61K 33/14; A61P 11/02
See application file for complete search history.

(56) References Cited

U.S. PATENT DOCUMENTS

| | | | |
|---|---|---|---|
| 6,419,821 B1 * | 7/2002 | Gadgil | B01D 39/2068 210/256 |
| 9,351,995 B1 | 5/2016 | Powers | |
| 2013/0156871 A1 | 6/2013 | Keller | |
| 2015/0104527 A1 | 4/2015 | Andro et al. | |
| 2019/0292075 A1 * | 9/2019 | Tax | C02F 1/461 |

FOREIGN PATENT DOCUMENTS

| | | |
|---|---|---|
| EP | 3 236 933 B1 | 11/2018 |
| GB | 2 481 407 A | 12/2011 |
| JP | H11-092394 A | 4/1999 |
| TR | 2012/10928 | 9/2012 |
| WO | 2006/125153 A2 | 11/2006 |
| WO | 2011/090932 A2 | 7/2011 |

OTHER PUBLICATIONS

International Search Report and Written Opinion of the International Searching Authority for International Patent Application No. PCT/TR2019/050993 mailed May 20, 2020, 9 pages.

* cited by examiner

*Primary Examiner* — Robert T. Crow
*Assistant Examiner* — John P Nguyen
(74) *Attorney, Agent, or Firm* — Bayramoglu Law Offices LLC

(57) ABSTRACT

The present invention relates to a nasal solution used for elimination of nasal occlusions, for cleaning of the inner section of the nose and for the treatment of nasal diseases, wherein bicarbonate ($HCO_3^-$) is provided with weight proportion between 0.05% and 1.50% and carbonate ($CO_3^{-2}$) is provided with weight proportion between 0.05% and 1.50% as the active substance in the ingredient thereof and it has alkali pH characteristic and preferably it is obtained from alkaline, closed basin natural spring waters.

2 Claims, No Drawings

NASAL SOLUTION WITH CLOSED BASIN NATURAL SPRING WATER CHARACTERISTIC AND METHOD FOR OBTAINING SAID NASAL SOLUTION

CROSS-REFERENCE TO RELATED APPLICATIONS

This application is a National Stage Application of PCT/TR2019/050993, filed 25 Nov. 2019, which claims the benefit of Serial No. 2018/18237, filed 29 Nov. 2018 in Turkey and Serial No. 2019/00230, filed 8 Jan. 2019 in Turkey and each of which applications are incorporated herein by reference. To the extent appropriate, a claim of priority is made to each of the above-disclosed applications.

TECHNICAL FIELD

The present invention relates to a pharmaceutical nasal solution obtained by means of stabilizing of preferably alkaline, closed basin natural spring waters and having alkali pH value and thus, having increased hypertonic effect since it comprises optimum proportion of bicarbonate ($HCO_3^-$) and carbonate ($CO_3^{-2}$) and a method for obtaining said solution. Moreover, the subject matter invention has adjustable alkali pH characteristic thanks to the pH agents provided in the formulations thereof.

PRIOR ART

Nasal (related to nose) solutions are used as one of the main items in the treatment of diseases like rhinitis, acute rhinosinusitis occurring due to viruses, in decreasing the secretions and bleedings, in elimination of the incrustations occurring after nasal surgeries and in elimination of the nasal occlusions. Moreover, nasal solutions function as the auxiliary item in the treatment of rhinitis, acute-chronic rhinosinusitis, allergic rhinitis, acute-chronic serozotitismedia and nasal polyposis. At the same time, nasal solutions can be used as the protective treatment in autumns and winters where the frequency of diseases increases.

In the present art, frequently, there are hypertonic-isotonic nasal solutions obtained from sea or ocean waters and used in a form like spray, drop, gel, etc.

In the present art, in the patent document with number US20150104527A1 and with title "Aqueous Ionic Solution Containing Sea water and at Least One Compound That Is Originally Immiscible with Sea Water", there is sea water ionic solution and similar items for usage in nose. Said sea water solution is a composition which has sea water by weight proportion between 30% and 98% and which has osmolality between 290 mOsm/kg and 400 mOsm/kg. The pH value of said solution is between 7 and 8.4. As the ingredient thereof, essentially sodium, potassium, chlorine, calcium and magnesium are provided.

In the present art, in a similar manner to the above mentioned sea water solution, there is the product mentioned in the patent document with number EP3236933A1 and with title "A Nasal Composition Containing Sea Water as Stability-Improving Excipient". The pH value of said solution is between 3 and 7. As the active substance in the ingredient of this nasal composition, xylometazoline hydrochlorine and ipratropium bromide are provided.

In the present art, in the patent specification with number US20130156871A1 and with title "Nasal Wash Solution", there is isotonic nasal solution comprising salt and having pH lower than 7 and similar items. In said isotonic solution, sodium ascorbate and sodium bicarbonate are used as pH buffer.

In the present art, in the patent document with number TR2012/10928 and with title "Composition of Natural Nasal Washing and Oral Rinse Solution and the Method for Preparation of Said Composition", a solution obtained from sea water is described. As the ingredient of said solution, "natural sea salt", sodium bicarbonate and xylitol are provided.

In the present art, the products comprising sodium chlorine and sodium bicarbonate are frequently used. The above mentioned nasal solutions are essentially obtained from sea and ocean waters. Within this context, in terms of the effect of input water and method of obtaining thereof, generally similar salt-based products are used.

In the present art, in the solution which is the subject of the patent specification with number GB2481407A and with title "A Rapid Onset Liquid Midazolam Composition for Buccal Administration", usage of carbonate and bicarbonate is described. In said document, the object of using carbonate and bicarbonate has been mentioned as the buffer function related to keeping the pH value at basic level in pharmacological application. However, said composition has not been developed for direct nasal usage, carbonate and bicarbonate are provided as auxiliary substance, and cyclodextrin and midazolame are used as the active substance. Moreover, no solution, related to obtaining of the solution from natural waters, has been described.

In the present art, in the patent document with number JP1999092394A and with title "Nose Drops Collunarium", a nasal solution, obtained from pigskin and collagen thereof, is described. In said document, it is described that sodium bicarbonate, soda ash and carbonate are used during washing of the animal skin for making of the animal skin suitable for usage.

As seen, in the present art, there is no nasal solution comprising bicarbonate ($HCO_3^-$) and carbonate ($CO_3^{-2}$) as active substance and which has hypertonic characteristic by means of the alkali pH value and obtained from preferably alkaline, closed basin natural spring waters.

OBJECTS AND ADVANTAGES OF THE INVENTION

The present invention relates to a nasal solution used for elimination of nasal occlusions, for cleaning of the inner section of the nose and for the treatment of nasal diseases, wherein bicarbonate ($HCO_3^-$) is provided with weight proportion between 0.05% and 1.50% and carbonate ($CO_3^{-2}$) is provided with weight proportion between 0.05% and 1.50% as the active substance in the ingredient thereof and it has alkali pH characteristic and preferably it is obtained from alkaline, closed basin natural spring waters.

The subject matter nasal solution has pH value between 7 and 11 and thus, it has hypertonic and alkali characteristic. Moreover, the most important characteristic of the present invention is the alkaline and alkali characteristics of the obtained nasal solution and thus, the subject matter has the characteristic of closed basin natural spring water and not sea (ocean) water. Thanks to said characteristics, when it is used as the main item in nasal occlusion treatment, it decreases the edema in the nose and it minimizes concha hypertrophy (nasal concha overgrowth). The subject matter nasal solution is effective in cleaning incrustation, clot and secretions which occur inside the nose after nasal surgeries.

Said nasal solution provides the infections to be taken under control thanks to the detergent effect which reduces surface tension and thanks to the favorable buffering effect of alkali pH. Within this context, the infection retards and secondary bacterial infection occurrence risk and frequency in the lower and upper respiratory paths is reduced. Thus, it helps in decreasing antibiotics usage which is a particularly serious problem in our country. Besides, it is also used for decreasing secretions in rhinitis and rhinosinusitis depending on viral reasons and for eliminating nose occlusion and for decreasing the viral load existing in the nose. In allergic rhinitis, the subject matter invention mechanically cleans the allergens accumulated in secretions inside the nose, prevents holding of the allergens inside the nose depending on the detergent effect and optimizes the immunological response given to the allergens and thus, decreases the clinical symptoms of the diseases. Moreover, it decreases the usage of local steroids and oral anti-histaminics used in the treatment.

Thanks to the detergent effect thereof, it mechanically cleans the mucopurulent secretions which increase in bacterial acute and chronic rhinosinusitis, and the frequency of these secretions is decreased and inflammation is reduced. Thus, it increases the efficiency of the antibiotic used and shortens the usage duration. Besides, it minimizes the usage of other chemical drugs (local and systemic decongestants, anti-histaminics, etc.) used in rhinosinusitis.

In the treatment of chronic and acute serozotitismedia; thanks to the characteristics of the solution sourced from the subject matter ingredient thereof, the subject matter solution decreases the edema of the Eustachian tube and facilitates drainage of the secretion from the middle ear. It provides elimination of secretion and occlusion formed in nasal polyposis thanks to the same effects.

The differences of the subject matter invention from other present products are as follows:
- It has alkali characteristic depending on the bicarbonate and carbonate existing in optimum proportion in the ingredient thereof
- Said alkali characteristic increases the effect of hypertonic water
- It has detergent effect depending on bicarbonate, carbonate and sulphate
- Thanks to said detergent effect, it decreases the surface tension inside the nose and provides contribution to the treatments.

Moreover, one of the important characteristics of the present invention is that said nasal solution is obtained preferably from alkaline, closed basin natural spring waters. In the preferred application of the present invention, in order to obtain said nasal solution, it is considered suitable that Van Lake water or Van Lake water simulation is used as the input water.

DETAILED DESCRIPTION OF THE INVENTION

The present invention essentially relates to a nasal solution comprising bicarbonate ($HCO_3^-$) with weight proportion between 0.05% and 1.50% and carbonate ($CO_3^{-2}$) with weight proportion between 0.05% and 1.50% and/or sodium ($Na^+$) with weight proportion between 0.1% and 1.60% and/or chlorine ($Cl^-$) with weight proportion between 0.1% and 2.43%.

Said nasal solution moreover comprises potassium ($K^+$) with weight proportion between 0% and 0.1% and/or magnesium ($Mg^{+2}$) with weight proportion between 0% and 0.1% and/or sulphate ($SO_4^{-2}$) with weight proportion between 0% and 0.8%.

Moreover, in the subject matter nasal solution, the mass proportion of bicarbonate ($HCO_3^-$)/sodium ($Na^+$) is between 0.4 and 1.9. In the same manner, the mass proportion of carbonate ($CO_3^{-2}$)/sodium ($Na^+$) is between 0.4 and 1.9.

Since there is bicarbonate ($HCO_3^-$) and carbonate ($CO_3^{-2}$) in the ingredient thereof, the pH value of the solution is 7 and greater, in other words, the solution becomes alkali. In the present invention, the preferred interval of said pH value is defined between 7 and 10. Bicarbonate and carbonate decrease the inner surface tension of the nose and they form detergent effect and provide formation of mucolytic effect.

Sodium ($Na^+$) and chlorine ($Cl^-$) provide healing effect on the nasal mucosa and eliminate occlusions. Potassium ($K^+$) provides repairing of the epithelial tissue in the respiratory path. Magnesium ($Mg^{+2}$) provides reduction of inflammations by providing reduction of the frequency of secretions. Sulphate ($SO_4^{-2}$) provides cleaning effect inside the nose.

In the table below, the substances provided inside the subject matter invention are given. The subject matter nasal solution can be formed from different combinations of the substances provided in the table.

| Ingredients | Amount (by weight) |
| --- | --- |
| Bicarbonate ($HCO_3^-$) | 0.05-1.50% |
| Carbonate ($CO_3^{-2}$) | 0.05-1.50% |
| Sodium ($Na^+$) | 0.1-1.60% |
| Chlorine ($Cl^-$) | 0.1-2.43% |
| Potassium ($K^+$) | 0-0.1% |
| Magnesium ($Mg^{+2}$) | 0-0.1% |
| Sulphate ($SO_4^{-2}$) | 0-0.8% |

The ingredient table of the preferred application of the subject matter nasal solution is as follows.

| Ingredients | Amount (by weight) |
| --- | --- |
| Bicarbonate ($HCO_3^-$) | 0.50% |
| Carbonate ($CO_3^{-2}$) | 0.80% |
| Sodium ($Na^+$) | 0.80% |
| Chlorine ($Cl^-$) | 1.01% |
| Potassium ($K^+$) | 0.05% (Optional) |
| Magnesium ($Mg^{+2}$) | 0.05% (Optional) |
| Sulphate ($SO_4^{-2}$) | 0.40% (Optional) |

Potassium ($K^+$), magnesium ($Mg^{+2}$) and sulphate ($SO_4^{-2}$) are provided optionally in the subject matter nasal solution and are provided in different combinations.

The substances, provided in the ingredient, exist in dissolved form in water during usage. The amounts, provided in the ingredient, define the proportional amounts in this solution.

Said nasal solution can be obtained from alkaline, closed basin, natural waters or artificially.

In the preferred application of the present invention, closed basin natural water, having the characteristics mentioned below, is used as input.

| Substances in the input (simulated) water | Amounts (by weight) |
| --- | --- |
| Bicarbonate ($HCO_3^-$) | %0.05-1.50 |
| Carbonate ($CO_3^{-2}$) | %0.05-1.60 |

-continued

| Substances in the input (simulated) water | Amounts (by weight) |
|---|---|
| Sodium (Na$^+$) | %0.1-1.60 |
| Chlorine (Cl$^-$) | %0.1-2.43 |
| Organic insoluble substances | %0-1 |

Van Lake can be shown as the best example to the alkaline, closed basin waters having the above mentioned characteristics. Production of the subject matter nasal solution by means of the water to be taken from Van Lake or by means of the water to be simulated in a similar manner to this water is considered as a preferred application. Besides, it is also possible that other natural waters with similar characteristics can be used or said nasal solution can be produced artificially. Thus, it is provided that the nasal solution has alkaline, closed basin natural spring water characteristic.

The process steps of the production method of the subject matter nasal solution by means of the above mentioned alkaline, closed basin natural water input are as follows:

For providing optimum ion concentration, the input water is mixed for 1-2 hours by adding external chemical substances; Said external chemical substances are Sodium carbonate (Na$_2$CO$_3$) and/or Sodium bicarbonate (NaHCO$_3$) and/or Sodium Chlorine (NaCl) and/or Magnesium sulphate (MgSO$_4$) and/or Magnesium chlorine (MgCl$_2$) and/or Potassium sulphate (K$_2$SO$_4$) and/or Potassium Chlorine (KCl). The External substances are added for preparing water with optimum ion concentration in case the ion concentration of the input water is lower than desired.

The input water is filtered by means of 200-2000 nanometer filter having application pressure between 3.5 and 4 bars and having operation capacity between 0-100 L/hour; this is applied for eliminating the organic dirts and suspended substances in micron level inside the input water.

After filtration of water, water is subjected to sterilization by means of UV lamp, and thanks to this, the microorganisms in the water are eliminated after filtration.

In different versions of the present invention, the following can be used as pH adjusting agents: Sodium carbonate (Na$_2$CO$_3$) and/or Sodium bicarbonate (NaHCO$_3$) and/or Potassium carbonate (K$_2$CO$_3$) and/or Potassium bicarbonate (KHCO$_3$) and/or Sodium tripolyphosphate (Na$_5$P$_3$O$_{10}$) alkali substances and/or CHES (Cyclohexyl-2-aminoethanesulphonic acid) and/or Glycine-Sodium hydroxide (NaOH) and/or TRIS (Hydroxy methyl aminomethane)-Hydrochloric acid (HCl) and/or Potassium dihydrogen phosphate (KH$_2$PO$_4$)-Sodium hydrogen phosphate (Na$_2$HPO$_4$) and/or Diethylbarbituric acid sodium acid-Hydrochloric acid (HCl) and/or Imidazole-Hydrochloric acid (HCl) and/or Triethanolamine+EDTA (Titriplex 3)-Hydrochloric acid (HCl) and/or Borax (H$_3$BO$_3$)+(Sodium Hydroksit) NaOH-Hydrochloric acid (HCl) buffers or the mixture combinations thereof. Thus, pH adjustment process can be realized between 7 and 11.

In the following examples, as the "nasal solution", solution comprising Bicarbonate (HCO$_3^-$), Carbonate (CO$_3^{-2}$), Sodium (Na$^+$) and Chlorine (Cl$^-$) having amounts provided in the preferred application has been defined.

Example 1

In order for the pH value of the nasal solution to be between 10 and 11, 0.6-1 grams of Sodium carbonate (Na$_2$CO$_3$) is added to the "nasal solution" of 1 liter.

Example 2

In order for the pH value of the nasal solution to be between 9 and 10.5, 0.3-0.7 grams of Sodium carbonate (Na$_2$CO$_3$) and 3-7 grams of Sodium tripolyphosphate are added to the "nasal solution" of 1 liter.

Example 3

In order for the pH value of the nasal solution to be between 8.5 and 9.75, 0.3-0.7 grams of Sodium carbonate (Na$_2$CO$_3$) and 3-7 grams of Sodium bicarbonate (NaHCO$_3$) are added to the "nasal solution" of 1 liter.

Example 4

In order for the pH value of the nasal solution to be between 10 and 11, 0.8-1.2 grams of Sodium carbonate (Na$_2$CO$_3$) and 0.1-0.25 grams of Sodium bicarbonate (NaHCO$_3$) are added to the "nasal solution" of 1 liter.

Example 5

In order for the pH value of the nasal solution to be between 7.5 and 8.5, 0.024-0.044 grams of Potassium dihydrogen phosphate (KH$_2$PO$_4$) and 1-1.5 grams of Sodium hydrogen phosphate (Na$_2$HPO$_4$) are added to the "nasal solution" of 1 liter.

Example 6

In order for the pH value of the nasal solution to be between 8.7 and 9.3, 0.80-1 grams of Borax (H$_3$BO$_3$) and 0.16-0.36 grams of Sodium Hydroxide (NaOH) are added to the "nasal solution" of 1 liter.

Example 7

In order for the pH value of the nasal solution to be between 9.5 and 10.5, 0.27-0.67 grams of Glycine and 0.25-0.65 grams of Sodium hydroxide (NaOH) are added to the "nasal solution" of 1 liter.

Example 8

In order for the pH value of the nasal solution to be between 8 and 9, 0.5-0.85 grams of Triethanol-amine and 0.1-0.35 grams of EDTA (Titriplex 3) and 17.5-27.5 ml 0.05 molar Hydrochloric acid (HCl) are added to the "nasal solution" of 1 liter.

What is claimed is:

1. A method of obtaining an alkaline and hypertonic nasal solution, the method comprising:
   filtering an input water through a 200-2000 nanometer filter having an application pressure between 3.5 and 4 bars and having operation capacity between 0-100 L/hour;
   sterilizing the filtered water by means of a UV lamp, wherein said input water comprises 0.9%-1.50% bicarbonate ($HCO_3^-$), 0.9%-1.50% carbonate ($CO_3^{-2}$) 0.1%-1.60% sodium ($Na^+$), and 0.1%-2.43% chlorine ($Cl^-$) by weight.

2. The method according to claim 1, further comprising adding one or more of magnesium sulfate, magnesium chloride, potassium sulfate, or potassium chloride to the input water and stirring the resulting mixture for 1-2 hours.

\* \* \* \* \*